(12) United States Patent
Jutila

(10) Patent No.: US 6,436,385 B2
(45) Date of Patent: *Aug. 20, 2002

(54) PREPARATION PROTECTING SKIN FROM MECHANICAL IRRITATION

(75) Inventor: Kirsti Jutila, Espoo (FI)

(73) Assignee: Cultor Corporation, Helsinki (FI)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/269,407

(22) PCT Filed: Sep. 25, 1997

(86) PCT No.: PCT/FI97/00577

§ 371 (c)(1), (2), (4) Date: Mar. 26, 1999

(87) PCT Pub. No.: WO98/13021

PCT Pub. Date: Apr. 2, 1998

(30) Foreign Application Priority Data

Sep. 26, 1996 (FI) .................................................. 963849

(51) Int. Cl.⁷ .............................................. A61K 31/74
(52) U.S. Cl. .................... 424/78.05; 424/400; 424/407; 424/78.05; 514/865
(58) Field of Search .............................. 424/78.05, 400, 424/401; 514/863

(56) References Cited

FOREIGN PATENT DOCUMENTS

| JP | 07309741 | 11/1995 |
|---|---|---|
| JP | 08020520 | 1/1996 |
| JP | 08081348 | 3/1996 |
| WO | 9118588 A1 | 12/1991 |
| WO | 91/18588 | * 12/1991 |
| WO | 9118588 | * 12/1991 |

OTHER PUBLICATIONS

Farage et al Skin Research and Technology 2001; 7:195–203, Development of a new test for mechanical irritation: behind the knee as a test site.
Mahmoud et al Contact Dermatitis 1984: 11: 179–185 Histological assessment of skin damage by irritants: its possible use in the evaluation of a barrier cream.
Hunter et al British J. of Dermatology (1974) 90, 481 Clinical and Laboratory Investigations Light and electron microscopic studies of physical injury to the skin.
Hunter et al British J. of Dermatology (1974) 90, 501 Tovell et al The action of sodium lauryl sulphate on rat skin —an ultrastructural study.
Berardesca et al Clinical Aspects Irritant Dermititis, New Clinical and Experimental Aspects Curr. Probl. Dermatol 1995 vol. 23, pp. 1–8 Mechanisms of Skin Irritation.
Hunter et al British J. of Dermatology (1974) 90, 491 Light and electron microscopic studies of physical injury to the skin.

* cited by examiner

Primary Examiner—Thurman K. Page
Assistant Examiner—Lakshmi Channavajjala
(74) Attorney, Agent, or Firm—Nixon & Vanderhye P.C.

(57) ABSTRACT

The invention relates to cosmetic preparations, particularly skin care products, shaving preparations, and depilatory preparations, which protect skin from mechanical irritation. The active agent contained in the preparations is trimethylglycine. The invention also relates to the use of trimethylglycine as a skin-protecting agent in different cosmetic preparations, and to a method of protecting skin from mechanical irritation.

9 Claims, 1 Drawing Sheet

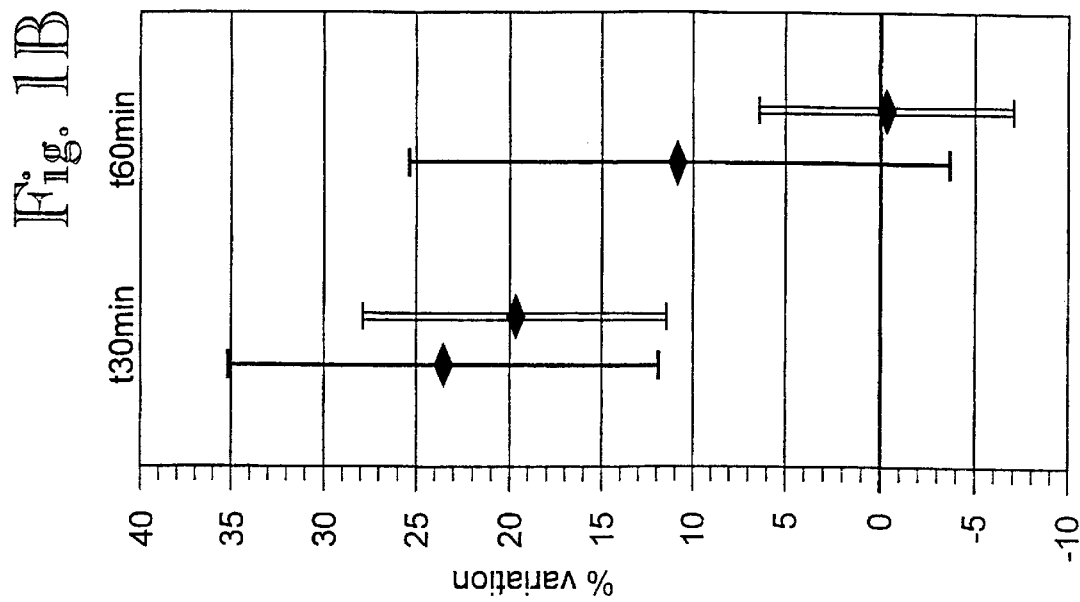
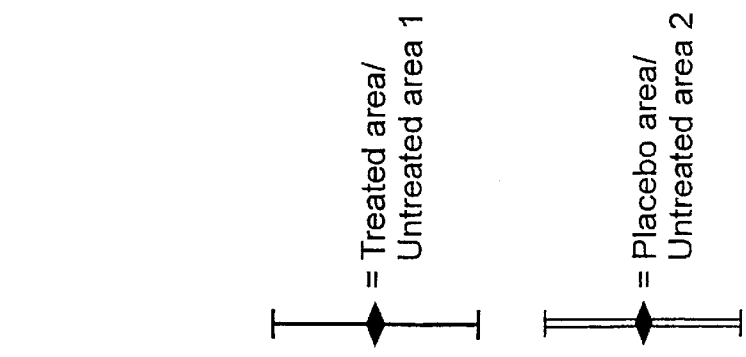
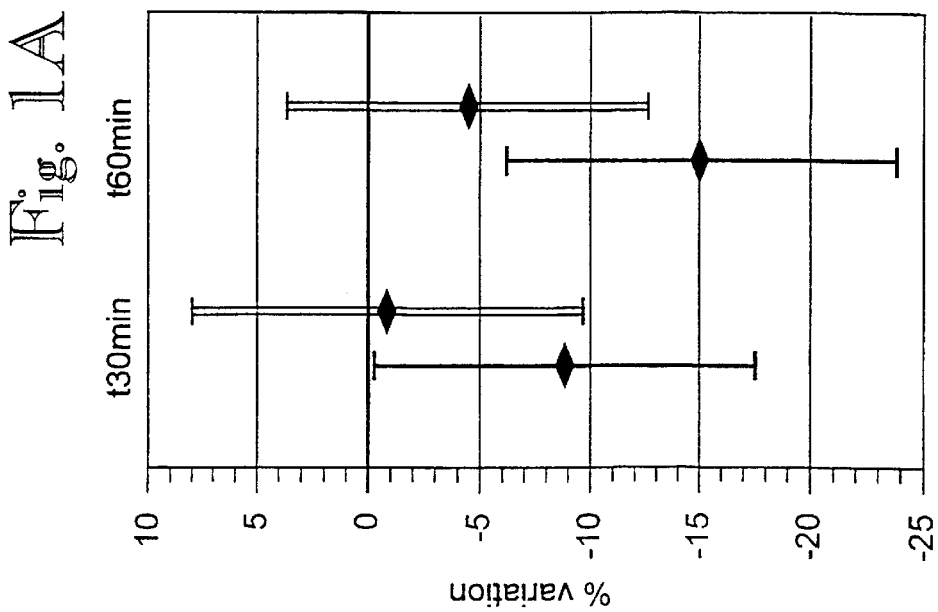

PREPARATION PROTECTING SKIN FROM MECHANICAL IRRITATION

This is a 35 U.S.C. §371 of PCT/FI97/00577, filed Sep. 25, 1997.

FIELD OF INVENTION

The present invention relates to cosmetic preparations, particularly to skin care products, shaving preparations, and depilatory preparations ('lady shaving' preparations), which protect skin from mechanical irritation. The active agent contained in the preparations is trimethylglycine. The invention also relates to the use of trimethylglycine as a skin-protecting agent in different cosmetic preparations, and to a method of protecting skin from mechanical irritation.

BACKGROUND OF INVENTION

Skin is subjected to mechanical irritation, i.e. it is scratched, abraded, chafed or cut, in many situations. When men shave, a razor or the blade of a shaver may scratch or cut. the skin on the face despite the use of shaving lather or shaving soap. Women, in turn, cut hair off the legs, armpits, and groin, where the skin is extra sensitive, and the treatment easily scrapes or cuts the skin. Infants and persons using incontinence diapers have the problem that their skin often moistens and thereby becomes thinner, and the diaper chafes and damages the skin. Shoes, in turn, abrade the skin on the heels, ball of the foot, and toes, and the skin on the hands is easily abraded and scratched in agricultural and garden work.

Cut, sore skin aches, smarts, and feels tight; microwounds are subjected to inflammation; and application of common cosmetic preparations to the skin does not necessarily ease the discomfort, nor protect the skin. On the contrary, application of a preparation on cut, sore skin often adds to smarting and skin irritation.

The object of the present invention is to provide a preparation protecting skin from mechanical irritation.

Another object of the present invention is to provide a method of protecting skin from mechanical irritation.

BRIEF DESCRIPTION OF INVENTION

Surprisingly, it has been discovered that trimethylglycine protects skin from cutting, scratching, abrasion, chafing, and other mechanical irritation, and so trimethylglycine can be used in different cosmetic preparations as an agent protecting skin from such irritation. The present invention thus relates to the use of trimethylglycine as an agent protecting skin from mechanical irritation in cosmetic preparations, particularly in skin care products, shaving preparations, and depilatory preparations. The present invention also relates to a cosmetic preparation that contains trimethylglycine as an ingredient protecting skin from mechanical irritation. The present invention further relates to a method of protecting skin from mechanical irritation by applying a trimethylglycine containing cosmetic preparation to the skin.

DETAILED DESCRIPTION OF INVENTION

In the present invention, mechanical irritation means external damage caused to epidermis by different objects, such as a shaver blade, a razor, shoes, a diaper, clothes, tools, or the like. A cosmetic preparation here means different skin care products, such as skin creams, cleansers, tonics, and milks; hand creams; foot care products, such as foot creams, and foot baths; shaving preparations, such as after-shave lotions, shaving lathers, foams, gels, and balms; depilatory preparations; products of personal hygiene ('lady-shaving' preparations), and the like. Preferred preparations according to the invention are foot care products, after-shave lotions, skin tonics, and baby care products.

In the present invention trimethylglycine means a naturally occurring quaternary ammonium type compound having the formula

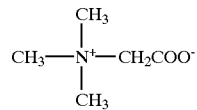

which is present as an anhydride or a monohydrate. The compound is commonly also called betaine, trimethylammonioacetate, 1-carboxy-N,N,N-trimethylmethaneaminium, inner salt, and glycine betaine. In the pure form, it is a white, crystalline compound that is readily soluble in water, and in lower alcohols, such as methanol and ethanol. In plants it functions as an osmolyte and thereby protects cells from the effects of osmotic stress.

Trimethylglycine has a bipolar structure, and it contains several metabolically reactive methyl groups, which it can donate in enzyme catalyzed reactions. Most organisms are able to synthesize small amounts of trimethylglycine, e.g. for the methyl donor function, but are not able to produce it, nor store it, in large amounts.

At cell level, trimethylglycine has been observed to protect plants particularly under stress conditions. It has been used as an agent improving the preservation characteristics of a plant, and as an agent improving the drought and chill resistance of a growing plant. To enhance growth, trimethylglycine has also been added to fertilizers. Further, trimethylglycine has been used as an additive in animal feed or fodder. It has also been observed to have pharmacological activity, e.g. it prevents detrimental effects of coccidiosis in broilers.

Synthetic long-chain alkyl ester, sulpho, and aluminium salt derivatives of trimethylglycine, commonly—and slightly misleadingly—called 'betaine derivatives' or 'betaines', have long been used as amphoteric surfactants in cosmetic industry, that is, e.g. as foaming agents in shampoos, soaps, and cleansers. As examples are mentioned U.S. Pat. Nos. 4,490,355 and 4,654,161. Trimethylglycine, instead, is not useful in the above-mentioned cosmetic applications, since its surface activity is completely different, and since it does not foam at all.

The surprising effect of trimethylglycine presented in the invention, i.e. that it protects skin from mechanical irritation, has not been described earlier, although trimethylglycine has been used for other purposes in cosmetic industry. EP 531,387 teaches that a preparation containing trimethylglycine reduces irritation caused by skin-irritating ingredients of a cosmetic preparation, such as cationic compounds, quaternary ammonium compounds, solvents, surfactants, and aseptic agents. EP 56,595 teaches a hair conditioning composition that contains 0.1 to 25% by weight of betaine, and 0.1 to 10% by weight of aliphatic organic acid, such as citric acid, and is stated to act as a hair conditioner, an antioxidant, and a buffer. German Patent 1,911,144 teaches a skin care composition that contains urea and lactic acid, and a cream base that can contain amino acid derivatives, such as betaine.

Trimethylglycine hydrochloride—since it is strongly acidic—differs in its characteristics from trimethylglycine anhydride and trimethylglycine monohydrate, has also been used in cosmetic products. Hungarian Patent T50,622 teaches a skin care composition that contains e.g. 0.3 to 0.6% of betaine hydrochloride.

EP 2,127 describes a shaving composition containing 'cosmetically acceptable betaine', which means particularly long-chain alkyl esters of glycine, the composition being stated to affect the root of a hair, so that the hair can be cut as close to the skin as possible, which improves the shaving result.

The best known organisms producing large amounts of trimethylglycine are plants of the genus Chenopodiaceae, such as sugar beet, and some microbes and marine invertebrates. It can be obtained e.g. from sugar beet by chromatographic methods. Trimethylglycine is commercially available both as an anhydride and as a monohydrate from Cultor Oy, Finnsugar Bioproducts.

A cosmetic preparation according to the present invention protecting skin from mechanical irritation contains 0.1 to 20% by weight, preferably 2 to 10% by weight, particularly 2 to 6% by weight of trimethylglycine as an anhydride or as a monohydrate in an aqueous composition or cream base, which may be e.g. an oil-in-water or a water-in-oil emulsion, water, or a water/alcohol mixture. The preparation also contains ingredients and additives that are commonly used in the cosmetic preparation concerned. They may be, for example, skin care agents, softening agents, astringent agents, refreshing agents, anti-oxidation agents, emulsifying agents, viscosity increasing agents, moisturizing agents, stabilizing agents, colouring agents, perfumes, surfactants, and the like, as well as alcohols and/or water.

The cosmetic preparations according to the invention include, in particular, skin care products, shaving preparations, depilatory preparations, and products of personal hygiene, such as skin tonics and milks; skin creams and lotions; cleansing creams, milks and gels; liquid cleansers; foot creams and baths; hand creams; refresher and moisturizing tissues and sprays; after-shave lotions; shaving lathers, gels and balms; and foam preparations. The preparation type is selected according to the need. The preparations of the invention can be formulated by common methods well known to those skilled in the art.

The use of trimethylglycine in the above preparations provides the products with characteristics that protect skin from mechanical irritation. As trimethylglycine also reduces the effect of any irritating agents contained in the cosmetic preparation, as described in EP 531,387, preparations containing trimethylglycine can be regarded as being particularly friendly to the skin.

It has been observed that trimethylglycine protects skin from mechanical irritation particularly effectively when it is applied as close as possible to the moment when the epidermis is cut, i.e. almost at the very moment that the damage is done. In the method of the invention for protecting skin from mechanical irritation, a preparation according the invention can thus be applied to the skin at the very moment that the skin is subjected to irritation, or even before it. For example, when one wants to protect the skin from being cut and scratched by the blade of a shaver during shaving or cutting off of hairs, a preferred preparation according to the invention might be a shaving lather or foam, to ensure that skin-protecting trimethylglycine is immediately present on the skin. If the preparation according to the invention is an after-shave lotion or a skin tonic, it will be applied to the skin immediately after shaving or cutting off of hairs. When one wants to protect the skin from being chafed by a diaper, a cream according to the invention can be applied to the skin before putting on a new diaper, or the skin can be washed or wiped with a cleanser or a moisturizing tissue according to the invention. Foot or hand creams according to the invention can be used according to the need for symptomatic alleviation of irritation, or for preventing irritation.

The invention will be described in greater detail by means of the following examples. The examples are only intended to illustrate the invention, and they are not to be regarded as restricting the scope of the invention in any way.

EXAMPLE 1

Effect of Trimethylglycine on Skin Irritation

The effect of trimethylglycine on the skin was studied by measuring the thermal conductivity of the skin by a method described by A. Dittmar in *Cutaneous investigation in health and disease. Non-invasive methods and instrumentation*, ed. J. L. Lévêque, Marcel Dekker Inc., New York-Basel, 1989. The method correlates directly with microcirculation on the skin. Thermal conductivity (K) is measured from the skin with a specific Hematron® thermal sensor and transformed into an electric signal, which is recorded by a recorder. In thermal conductivity ($\Delta K$), a significant level of variation is 0.1 mW/cm·° C.

The test was conducted on two test groups, each one of which comprised six healthy female volunteers. In the first test group (group 1), four cutaneous test areas were defined on the arm of each subject, and microcirculation was first measured for 30 minutes before the preparation was added. The skin was then cut by scraping in all the four areas, and onto the skin was pressed a filter paper into which a solution had been absorbed that contained 14 $\mu$l/cm$^2$ of 4% (weight/volume) trimethylglycine in distilled water, or only distilled water (placebo). Subsequently, microcirculation was measured for 60 minutes at the erythematous, damaged points on the skin, treated with the solution.

In the second test group (group 2), the subjects' microcirculation was measured at the erythema in the same way as above, but the irritation was here caused by 30-minute infrared irradiation (IR Philips 250 S lamps, spectrum 700 to 2500 nm, power 250 W, light energy 70 mW/cm$^2$, irradiation area 14 cm$^2$) in the four cutaneous areas defined on the upper back.

The thermal conductivity values measured on each volunteer subject are shown in table 1 (group 1) and table 2 (group 2). Tables 1 and 2 show the mean values (n=6) of thermal conductivity (K expressed as mW/cm·° C.) in the treated area, placebo area, and untreated areas at different instances of measuring. In tables 1 and 2, the treated area means an area treated with a preparation containing trimethylglycine; untreated area 1 is an untreated area that is symmetric with the area treated with the preparation containing trimethylglycine; the placebo area means an area treated with a placebo; and untreated area 2 is an untreated area that is symmetric with the area treated with the placebo.

TABLE 1

Mean values of thermal conductivity (K), expressed as mW/cm · ° C., in mechanical skin irritation

| | time t0[1] | t30[2] | t60[3] |
|---|---|---|---|
| treated area | 3.82 ± 0.59 | 3.66 ± 0.69 | 3.42 ± 0.41 |
| untreated area 1 | 3.57 ± 0.27 | 3.77 ± 0.22 | 3.91 ± 0.29 |
| placebo area | 3.94 ± 0.48 | 3.82 ± 0.23 | 3.81 ± 0.18 |
| untreated area 1 | 3.28 ± 0.28 | 3.36 ± 0.34 | 3.50 ± 0.23 |

TABLE 2

Mean values of thermal conductivity (K), expressed as mW/cm · ° C., in thermal skin irritation

|  | time t0[1] | t30[2] | t60[3] |
|---|---|---|---|
| treated area | 3.13 ± 0.30 | 3.85 ± 0.31 | 3.60 ± 0.38 |
| untreated area 1 | 3.61 ± 0.25 | 3.68 ± 0.22 | 3.84 ± 0.26 |
| placebo area | 3.45 ± 0.21 | 3.74 ± 0.27 | 3.26 ± 0.20 |
| untreated area 2 | 3.72 ± 0.29 | 3.46 ± 0.32 | 3.58 ± 0.36 |

[1]before application of product
[2]30 min after application of product
[3]60 min after application of product
treated area = area treated with product Per cent (%) variations between the treated area and untreated area 1, and the placebo area and untreated area 2 were calculated for each volunteer subject 30 and 60 min after application of the product. The variations were calculated using the formula $$\% \text{ var} = \frac{(TZ_i - TZ_0) - (NTZ_i - NTZ_0)}{TZ_0 + (NTZ_i - NTZ_0)} \cdot 100$$

where $TZ_i$=treated area or placebo area at time instant t30 or t60
$TZ_0$=treated area or placebo area at time instant t0
$NTZ_i$=untreated area 1 or untreated area 2 at time instant t30 or t60
$NTZ_0$=untreated area 1 or untreated area 2 at time instant t0.

The mean values of the per cent variations and the standard errors of the mean values (n=6) in group 1 and group 2 are shown in tables 3 and 4, respectively.

TABLE 3

% Variation, group 1

|  | t30 min | t60 min |
|---|---|---|
| treated area/untreated area 1 | −8.9 ± 8.6 | −15.0 ± 8.8 |
| placebo area/untreated area 2 | −0.8 ± 8.9 | −4.6 ± 8.2 |

When a preparation containing trimethylglycine, diluted at a concentration of 4% (weight/volume) in distilled water, was applied to the skin, microcirculation reduced (mean variation: −8.9±8.6%) after 3Q min. An even more significant reduction in the microcirculation was achieved after 60 minutes of treatment (mean variation: −15.0±8.8%).

In the placebo area, the microcirculation does not vary 30 and 60 min after treatment.

TABLE 4

% Variation, group 2

|  | t30 min | t60 min |
|---|---|---|
| treated area/untreated area 1 | 23.5 ± 11.8 | 10.8 ± 14.5 |
| treated area/untreated area 2 | 19.7 ± 8.2 | −0.6 ± 6.7 |

When a preparation containing trimethylglycine, diluted at a concentration of 4% (weight/volume) in distilled water, was applied to the skin, microcirculation increased (mean variation: 23.5±11.8%) after 30 min. No variation was observed in the microcirculation 60 min after the treatment (mean variation: +10.8±14.5%).

In the placebo area, microcirculation increased 30 min after the treatment (mean variation: +19.7±8.2), but 60 min after the treatment, no variation was observed in the microcirculation (mean variation: −0.6±6.7).

As compared with the placebo, a preparation containing trimethylglycine diluted at a concentration of 4% (weight/volume) in water was effective against mechanical erythema (group 1) after normal application. The effect was detected 60 min after the application. The results show that the preparation is effective against skin irritation when the damage is relatively superficial. In addition, cutting of the skin causes erythema and probably enhances penetration of the preparation, which in turn adds to the effect of the preparation.

Instead, a preparation containing trimethylglycine had no effect on thermal erythema (group 2). No problems arose in respect of sensitivity in either of the tests: the subjects tolerated the trimethylglycine preparation well.

FIGS. 1A (group 1) and 1B (group 2) are diagrams drawn on the basis of the results.

EXAMPLE 2

This example describes different preparations according to the present invention.

| Baby lotion 1 | |
|---|---|
| Mineral oil | 26.00% |
| Lanolin | 1.04% |
| Stearic acid | 0.94% |
| Triethanolamine | 0.52% |
| Water | 65.68% |
| Tnmethylglycine | 4.00% |
| Stearyl alcohol | 0.94% |
| Cetyl alcohol | 0.52% |
| Sodium alginate | 0.36% |
| Perfume | q.s. |
| Baby lotion 2 | |
| Cetyl stearyl alcohol | 1.00% |
| Mineral oil | 4.00% |
| Polysorbate 60 | 1.70% |
| Sorbitan isostearate | 1.00% |
| Glyceryl stearate | 1.00% |
| Liquid lanolin | 0.25% |
| Water | 81.35% |
| Trimethylglycine | 4.00% |
| Hydroxyethyl cellulose | 0.20% |
| Glycerine | 5.50% |
| Perfume, preservative | q.s. |
| Foot cream 1 | |
| Glyceryl monostearate | 15.00% |
| Lanolin | 1.00% |
| Sorbitol syrup, 70% | 2.50% |
| Glycerine | 2.50% |
| Antimicrobial agent | 0.25–0.50% |
| Trimethylglycine | 4.00% |
| Water | balance 100.00% |
| Foot cream 2 | |
| Glyceryl monostearate | 12.0% |
| Mineral oil | 2.0% |
| Glycerine | 3.0% |
| Spermaceti substitute | 5.0% |
| Camphor | 1.0% |
| Methyl salicylate | 1.0% |
| Water | 69.9% |

-continued

| | |
|---|---|
| Trimethylglycine | 6.0% |
| Preservative | 0.1% |

Foot cream 3

| | |
|---|---|
| Ottasept extra | 1.00% |
| Lexemul AR | 16.00% |
| Cetyl alcohol | 1.00% |
| Amerchol L-101 | 3.00% |
| Solulan 98 | 0.50% |
| Mineral oil | 3.00% |
| Alcloxa | 0.25% |
| Propyfene glycol | 5.00% |
| Distilled water | 65.95% |
| Trimethylglycine | 4.00% |
| Perfume | 0.3% |

Bay salt foot bath

| | |
|---|---|
| Potassium iodide | 1 part |
| Potassium bromide | 2 parts |
| Magnesium chloride | 250 parts |
| Calcium chloride | 125 parts |
| Magnesium sulphate | 250 parts |
| Sodium sulphate | 500 parts |
| Sodium chloride | 1500 parts |
| Trimethylglycine | 500 parts |
| Colouring agent, perfume | q.s. |

Foot bath

| | |
|---|---|
| Cocamidopropylbetaine | 45% |
| Aminoxid WS35 | 3% |
| Cocamidopropylaminoxide | 3% |
| TEGO 103S | 5% |
| Undecylene diethanolamide | 2% |
| Lactic acid | 5% |
| Trimethylglycine | 10% |
| Water | 30% |
| Perfume | q.s. |

After-shave lotion

| | |
|---|---|
| Ethyl alcohol, denatured | 56% |
| Propylene glycol | 3% |
| Trimethylglycine | 4% |
| Water | 36% |
| Perfume | 1% |

Astringent after-shave gel

| | |
|---|---|
| Dipotassium glycyrrhizinate | 1.0% |
| Citric acid | 0.5% |
| Zinc sulphate | 0.2% |
| Zinc phenol sulphonate | 0.2% |
| Ethyl alcohol | 10.0% |
| Propylene glycol | 5.0% |
| Trimethylglycine | 2.0% |
| Water | 81.8% |
| Perfume preservative | q.s. |

-continued

Soap-free after-shave cream

| | |
|---|---|
| Glyceryl monostearate SIE | 10.0% |
| Mineral oil | 10.0% |
| Vaseline | 6.0% |
| Tegiloxan 100 | 0.5% |
| Lanolin | 3.0% |
| Cetyl alcohol | 3.0% |
| Glycerol | 3.0% |
| Citric acid | 0.2% |
| Potassium aluminium sulphate | 0.1% |
| Trimethylglycine | 4.0% |
| Water | 60.2% |
| Perfume | q.s. |

What is claimed is:

1. A method of protecting skin from mechanical irritation selected from irritation induced by scratching, abrasion, chafing and scraping, said method comprising applying to the skin a cosmetic preparation containing a skin protecting effective amount of trimethyiglycine as an anhydride or a monohydrate.

2. A method of protecting skin from mechanical irritation selected from irritation induced by scratching, abrasion, chafing and scraping, said method comprising applying to the skin before or at the time the skin surface is subjected to mechanical irritation a cosmetic preparation containing a protective amount of trimethylglycine as an anhydride or a monohydrate.

3. The method according to claim 1 or 2 wherein the cosmetic preparation contains trimethylglycine in a concentration of 0.1 to 20% by weight, based on the weight of the preparation, in a suitable cosmetic base.

4. The method of claim 3 wherein the concentration is 2 to 10% by weight.

5. The method of claim 4 wherein the concentration is 2 to 6% by weight.

6. The method according to claim 1 or 2 wherein the cosmetic preparation is a skin care product, a shaving preparation or a depilatory preparation.

7. The method according to claim 1 or 2, wherein the cosmetic preparation is a foot care product or a hand cream.

8. The method according to claim 1 or 2 wherein the cosmetic preparation is a baby care product.

9. The method according to claim 1 or 2 wherein the cosmetic preparation is an after-shave lotion or a skin tonic.

* * * * *

UNITED STATES PATENT AND TRADEMARK OFFICE
CERTIFICATE OF CORRECTION

PATENT NO. : 6,436,385 B2
DATED : August 20, 2002
INVENTOR(S) : Jutila

It is certified that error appears in the above-identified patent and that said Letters Patent is hereby corrected as shown below:

<u>Title page,</u>
Item [73], delete, "[73] Assignee: Cultor Corporation
                                    Helsinki Finland"
and insert -- [73] Assignee: Finnfeeds Finland Oy
                                Espoo, Finland --

Signed and Sealed this

Twenty-fifth Day of November, 2003

JAMES E. ROGAN
*Director of the United States Patent and Trademark Office*